(12) United States Patent
Vogler et al.

(10) Patent No.: US 8,235,973 B2
(45) Date of Patent: Aug. 7, 2012

(54) DEVICE FOR LASER-OPTICAL EYE SURGERY

(75) Inventors: Klaus Vogler, Eckental/Eschenau (DE); Olaf Kittelmann, Nuernberg (DE)

(73) Assignee: Wavelight AG, Erlangen (DE)

( * ) Notice: Subject to any disclaimer, the term of this patent is extended or adjusted under 35 U.S.C. 154(b) by 199 days.

(21) Appl. No.: 12/426,831

(22) Filed: Apr. 20, 2009

(65) Prior Publication Data

US 2009/0299347 A1 Dec. 3, 2009

(30) Foreign Application Priority Data

Apr. 22, 2008 (EP) .................................... 08007790

(51) Int. Cl.
*A61F 9/008* (2006.01)
(52) U.S. Cl. ........................................... 606/5; 128/898
(58) Field of Classification Search .................. 606/4, 5, 606/107, 166; 607/53
See application file for complete search history.

(56) References Cited

U.S. PATENT DOCUMENTS

| | | | |
|---|---|---|---|
| 4,907,586 A * | 3/1990 | Bille et al. | 606/5 |
| 6,585,723 B1 * | 7/2003 | Sumiya | 606/5 |
| 2004/0199150 A1 * | 10/2004 | Lai | 606/5 |
| 2005/0024586 A1 * | 2/2005 | Teiwes et al. | 351/209 |
| 2005/0228366 A1 * | 10/2005 | Kessler et al. | 606/5 |
| 2007/0032782 A1 * | 2/2007 | Youssefi et al. | 606/11 |
| 2007/0282313 A1 * | 12/2007 | Huang et al. | 606/5 |
| 2008/0058780 A1 * | 3/2008 | Vogler | 606/5 |
| 2008/0278687 A1 * | 11/2008 | Somani | 351/208 |
| 2009/0118718 A1 * | 5/2009 | Raksi et al. | 606/5 |

FOREIGN PATENT DOCUMENTS

EP 0 983 757 A 3/2000

* cited by examiner

*Primary Examiner* — Henry M Johnson, III
(74) *Attorney, Agent, or Firm* — Haynes and Boone, LLP

(57) ABSTRACT

A device for laser-optical eye surgery includes a source (10) of pulsed femtosecond laser radiation and also optical components (12, 14, 16) for guiding the laser radiation and focusing the same onto a treatment location on or in the eye (28), the optical components including a plurality of lenses (18, 20) arranged in succession in the beam path of the laser radiation. In accordance with the invention, at least one (18) of the lenses is arranged so as to be adjustable relative to other lenses in the direction of the beam path. In particular, the adjustable lens is a first diverging lens of beam-expansion optics (12). An actuating arrangement (24) is assigned to the adjustable lens for its adjustment, for the control of which arrangement a control unit (26) is provided which is set up to access measured data concerning the topography of a surface of the eye and to control the actuating arrangement in a manner depending on the measured surface topography. The laser device enables the abandonment of a contact lens to be placed onto the eye.

18 Claims, 2 Drawing Sheets

DEVICE FOR LASER-OPTICAL EYE SURGERY

Figure 1:
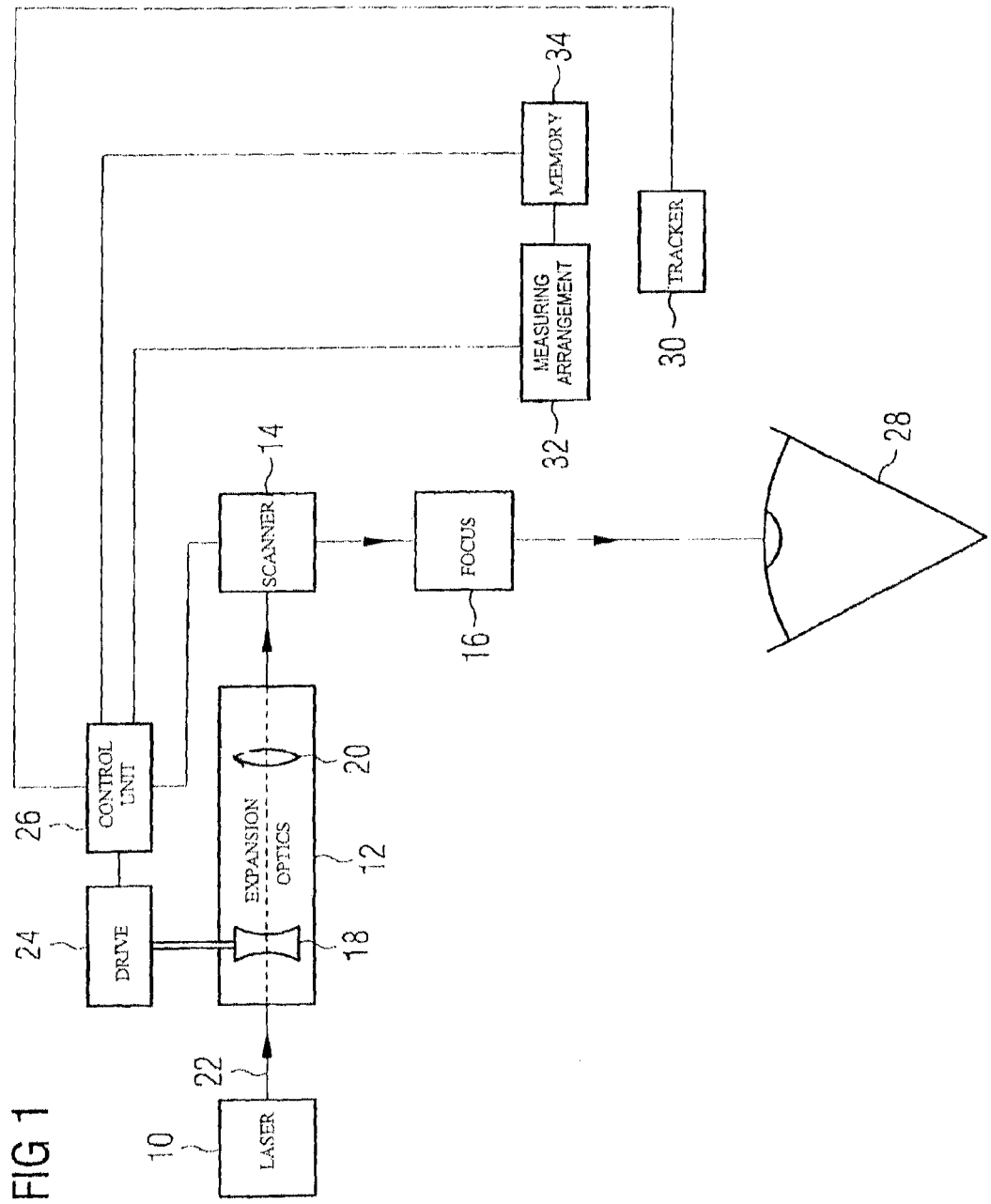

This application claims priority to European Patent Application No. EP 08 007 790.2 filed 22 Apr. 2008, the entirety of which is incorporated by reference herein.

The invention relates to a device for laser-optical eye surgery.

Lasers are employed in eye surgery in a variety of ways. For example, in refractive eye surgery, which serves for eliminating visual disorders of the eye, incisions frequently have to be introduced into the cornea or into the lens. A widespread technique in this connection is so-called femtoLASIK. In the case of LASIK (laser in-situ keratomileusis), a superficial small disc is firstly cut out of the cornea. This small disc, which in the specialist field is designated as a flap, is still attached to the remaining epithelial tissue in a hinged region; it is folded aside, in order in this way to expose the underlying tissue regions of the cornea. Material is then excised from the stroma by means of an excimer laser in accordance with a previously ascertained ablation profile. After this, the flap is folded back, and it heals with the remaining tissue in a relatively short time. Traditionally the flap is produced mechanically by means of a microkeratome. Less injurious, however, is production by means of a laser. For this purpose, laser radiation with ultrashort pulse durations in the femtosecond range is employed (hence femtoLASIK). For a precise localisation of the incision, a comparatively small focus diameter with a short Rayleigh length is required. Typical focus diameters in connection with the introduction of flap incisions or other incisions in the cornea or in the lens of the eye amount to about 5 μm or below. Conventional Rayleigh lengths amount to about 10 μm or below.

The influencing of material and the alteration thereof take place substantially only in the region of the beam focus. Outside of the beam focus the energy density is too low. On account of the small focus dimensions, a precise focusing of the laser beam to the desired location at which an incision is to be made is required. The precise setting of the focus location in the x-y plane (this is understood to mean the plane perpendicular to the beam axis) is possible with a deflecting unit (scanner) consisting of one or more deflecting mirrors which are adjustable in controlled manner. However, problems are associated with the focus control in the z-direction (i.e. in the direction of the beam axis). If, for example, it is desired to avoid a z-adjustment of the beam focus in the course of a surface incision that is to extend in the cornea at least partly at constant depth (as is the case with a flap), an applanation plate that is flat on the side facing towards the eye has to be placed onto the eye, in order in this way to press the cornea flat. The flap can then be produced by means of a planar surface incision.

In this case the applanation plate is fixed in relation to the objective focusing the laser radiation, and in this way provides a z-reference for the beam focus. But as a result of the eye being pressed flat the intraocular pressure unfortunately increases appreciably, which under certain circumstances can even lead to irreversible damage to the optic nerve.

Slighter deformations of the eye are possible if use is made of a contact lens that is concavely shaped on its side facing towards the eye. However, even with such lenses deformations of the eye can never be completely avoided. In addition, dished contact lenses normally have a negative influence on the quality of the beam focus. The curved interface between contact lens and cornea may, for example, result in comatic distortions, which in turn may have an unfavourable effect on the quality of the incision.

It is therefore the object of the invention to create a device for laser-optical eye surgery that permits a considerate yet precise treatment of the eye.

In achieving this object, the invention starts from a device for laser-optical eye surgery, with a source of pulsed femtosecond laser radiation and also with optical components for guiding the laser radiation and focusing the same onto a treatment location on or in the eye, the optical components including a plurality of lenses arranged in succession in the beam path of the laser radiation. In accordance with the invention, according to one approach at least one of the lenses is arranged so as to be adjustable relative to other lenses in the direction of the beam path, whereby an actuating arrangement is assigned to the adjustable lens for its adjustment, and for the purpose of controlling the actuating arrangement a control unit is provided that is set up to access measured data concerning the topography of a surface of the eye and to control the actuating arrangement in a manner depending on the measured surface topography.

The solution according to the invention is based on a z-control of the beam focus in a manner depending on a measured surface topography of the eye. It permits a contact lens placed onto the eye to be dispensed with, be it in the form of a planar applanation plate or in the form of a concavely dished lens. The complete abandonment of such a contact lens accordingly has the consequence that no undesirable deformations of the eye of any kind arise in the course of the treatment; neither do optical distortions arise by reason of the contact lens. In particular, the topographical measured data represent the topography of the outer corneal surface.

However, it will be understood that, in principle, it is conceivable to use a different surface within the eye by way of reference surface to be surveyed, for example the lens surface.

The topography of the surface of the eye can be measured, for example, with light-slit technology, by means of ultrasound or by means of optical coherence tomography. These technologies are known as such in the specialist field, for which reason no further explanations relating to the manner of acquiring the topographical measured data are needed here. A measuring arrangement operating in accordance with one or more of the stated measuring principles may be part of the device according to the invention and may save its measured data in a memory to which the control unit has access.

To the extent that recourse is had to optical coherence tomography for the topographical measurement, the invention teaches, in particular, the use of extremely fast devices for optical coherence tomography using femtosecond radiation-sources, preferably with repetition-rates in the region of 10 GHz and preferably in the region of 100 GHz or more, for example the use of so-called VECSELs (vertical external-cavity surface-emitting lasers). Such semiconductor laser diodes can be pumped electrically or optically and attain very high outputs and efficiencies, despite a physical size in the centimeter range. Femtosecond fibre lasers may also be employed within the scope of optical coherence tomography. Such radiation-sources can generate fs supercontinua with bandwidths greater than 100 nm up to 1000 nm and with repetition-rates greater than 100 GHz, so that an extremely high measuring-rate can be attained which, where required, permits a virtually real-time measurement of the topography of the reference surface (for example, the corneal surface) during the surgical procedure. Accordingly, the topographical measurement does not necessarily have to be carried out completely prior to the operation but can be carried out during the operation, 'online' as it were.

The optical components of the device according to the invention are expediently constituted by beam-expansion optics, a scanning unit arranged downstream of the beam-expansion optics in the direction of the beam path and serving for beam scanning in a plane transverse to the beam direction, and also focusing optics arranged downstream of the scanning unit in the direction of the beam path. The beam-expansion optics expand the laser beam sufficiently in order to achieve the high numerical aperture of the focusing optics that is needed for the small focus diameters being striven for. The beam-expansion optics will normally include several lenses arranged in succession in the beam direction, of which at least one takes the form of a diverging lens and at least one other takes the form of a converging lens, the diverging lens being situated upstream of the converging lens. Conventional beam-expansion optics on the market consist, as a rule, of a total of two or three lenses, of which the first lens (input lens) is always a diverging lens. Its diameter is substantially smaller than that of the subsequent converging lens(es). Accordingly, its mass is also normally considerably lower than that of the subsequent converging lens(es) of the beam-expansion optics. For this reason, a preferred embodiment of the invention provides to arrange a diverging lens of the beam-expansion optics, in particular the input lens of the beam-expansion optics, in adjustable manner and to displace it for the purpose of the z-control of the beam focus relative to at least one converging lens of the beam-expansion optics in the beam direction. In this case the low mass of the diverging lens enables a highly dynamic adjustment of the same, for example by means of an electromotive or piezoelectric actuating drive. On the other hand, in the case of an adjustment of the subsequent converging lens or even of the focusing optics, the mass to be moved would be incomparably greater, and this would be detrimental to the desired dynamics.

It has become evident that, given suitable design and positioning of the lenses of the device according to the invention, an adjusting distance of the input lens of the beam-expansion optics of 10.0 mm can suffice in order to be able to displace the beam focus within a range of 1.4 mm. As a rule, this is sufficient in order to compensate for the convexity of the cornea and to introduce into the cornea a two-dimensional incision that is situated at constant depth.

The control unit may have been set up to ascertain a nominal position for the adjustable lens in a manner depending on the measured surface topography and also in a manner depending on a height distance of a desired location of action of the radiation in the eye from the topographically surveyed surface and to control the actuating arrangement in a manner depending on the ascertained nominal position. The height distance in this connection relates to the spacing in the z-direction. Even with a perfectly stationary head posture and even with fixation of the eye by means of a suction ring, slight movements of the cornea in the z-direction cannot be completely avoided. Such movements are, for example, due to respiration. In order nonetheless to be able to position the beam focus always precisely at the desired place in the eye, in a preferred further development the device according to the invention is equipped with a measuring arrangement that is set up to detect displacements of the height position of at least one reference location on or in the eye. In this case the control unit is set up to correct the ascertained nominal position of the adjustable lens in a manner depending on the detected current height position of the at least one reference location and to control the actuating arrangement in a manner depending on the corrected nominal position. The corneal vertex, for example, enters into consideration by way of reference location.

In the case where a suction ring for fixing the eye is dispensed with, even with otherwise stationary head posture rotational movements of the eyeball are normally unavoidable. Such movements of the eye may also necessitate a z-correction of the ascertained nominal position for the adjustable lens, because a rotation of the eyeball can simultaneously bring about a displacement of the z-coordinate of a desired location of action of the laser radiation in the eye. Therefore the device according to the invention may include a measuring arrangement that is set up to detect movements of at least one reference location on or in the eye in a plane transverse to the direction of the beam path, the control unit being set up to correct the nominal position of the adjustable lens in a manner depending on the detected current transverse position of the at least one reference location and to control the actuating arrangement in a manner depending on the corrected nominal position.

Irrespective of whether rotational movements of the eye are taken into account or not in the correction of the nominal position of the adjustable lens, in every case a control of the beam-scanning unit (scanner) in a manner depending on the movements of the eye is required, in order to be able to track the beam focus precisely at all times. Monitoring systems (eye trackers) suitable for this are known as such in the specialist field. For example, in this connection the corneal vertex may be monitored for displacements transverse to the beam axis.

The focus diameter of the laser radiation is preferably not greater than about 10 μm, better not greater than about 7 μm, and still better not greater than about 5 μm. The Rayleigh length of the laser radiation is preferably not greater than about 20 μm, better not greater than about 15 μm, and still better not greater than about 10 μm.

For the production of a two-dimensional incision in the cornea that is substantially parallel to the corneal surface by line scanning, the control unit may have been set up to provide to the actuating arrangement a control signal with approximate triangular characteristic and with varying triangle height. As an alternative to a line scanning, in which the beam is moved over the eye in parallel lines, a spiral scanning is conceivable. In this case, for the production of a two-dimensional incision in the cornea that is substantially parallel to the corneal surface by spiral scanning, the control unit may have been set up to provide to the actuating arrangement a control signal of monotonically variable amplitude. The triangular shape of the control signal in the case of line scanning is linked to the fact that each line extends from the subjacent cornea margin via superjacent intermediate regions and back to the corneal margin. Correspondingly, the lens has to be set in differing positions. The varying triangle height of the control signal originates from the fact that in the case of lines that extend over the corneal vertex or close to the same the z-travel of the lines is greater, on account of the convexity of the cornea, than in the case of lines close to the margin. In the case of spiral scanning, on the other hand, a continual adjustment of the adjustable lens in one direction is required, this being expressed in the monotonically variable amplitude of the control signal.

The device according to the invention not only does not need a contact lens to be placed onto the eye, it is preferentially also free from mounting structures for such a contact lens.

According to a further aspect, the invention provides a control method for a device for laser-optical eye surgery, the device including a source of pulsed femtosecond laser radiation, a plurality of lenses arranged in succession in the beam path of the laser radiation, of which at least one is arranged so as to be adjustable in the direction of the beam path relative to other lenses, and also an actuating arrangement for adjusting the at least one adjustable lens. In accordance with the invention, in the method a nominal position for the adjustable lens is ascertained on the basis of stored topographical measured data, and a control signal for the actuating arrangement is generated in a manner depending on the ascertained nominal position.

Figure 2:
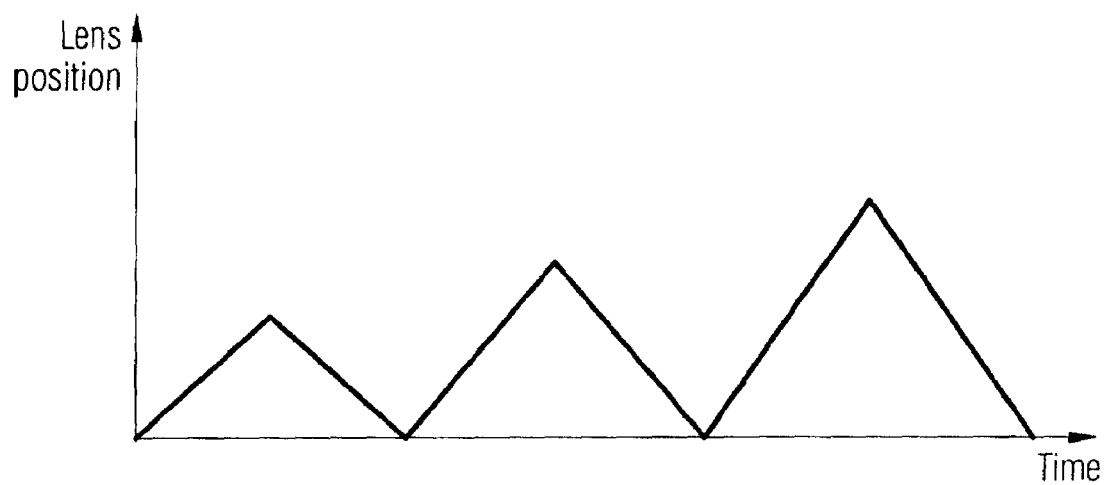
Figure 3:
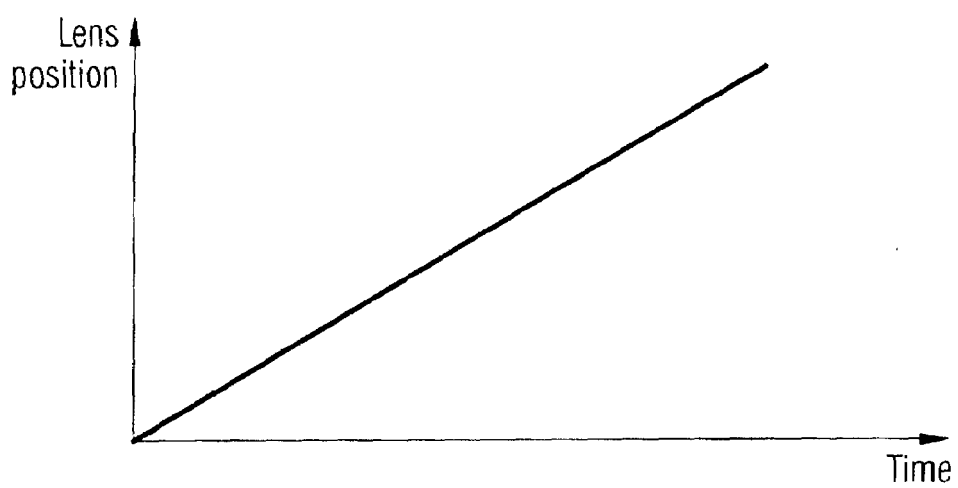

The invention will be elucidated further in the following on the basis of the appended drawings. Shown are:

FIG. 1 a schematic block representation of an exemplary embodiment of a device for laser-optical eye surgery, FIG. 2 a qualitative progression of the actuating position of an individually adjustable lens of the laser device of FIG. 1 in the case of a line scan and FIG. 3 a qualitative progression of the actuating position of the adjustable lens in the case of a spiral scan.

The laser device for eye surgery shown in FIG. 1 includes a laser generator 10 which generates and outputs pulsed laser radiation with a pulse duration in the femtosecond range. The term 'femtosecond' is to be understood broadly here; it is not to be understood in the sense of a sharp delimitation in relation to pulse durations starting from 1 ps. Quite the reverse: the invention is also suitable in principle for pulse durations longer than 1 ps. The reference to a pulse duration in the fs range is directive solely to the extent that fs lasers employed in eye surgery ordinarily have comparatively small focus dimensions with a focus diameter of, for example, at most 5 μm and with a Rayleigh length of at most 10 μm and the invention displays its advantages especially in the case of such small focus dimensions. Nevertheless, the pulse duration of the laser radiation preferentially lies below 1 ps, for example in the region of three-digit femtoseconds.

The pulse-repetition rate of the laser generator 10 may, for example, lie within the two-digit or three-digit kHz range right up to the MHz range. In particular, the pulse-rate of the laser generator 10 may be controllable. The wavelength of the laser radiation that is generated and employed for the purpose of treatment may, for example, lie in the infrared region, round about 1 μm, but it may also be shorter, right down to the UV region.

In the beam path of the laser beam that is output by the laser generator there follow, in succession, beam-expansion optics 12, a scanner 14 and also focusing optics 16. The beam-expansion optics 12 here are represented as a two-lens system with a diverging lens 18 and with a converging lens 20 situated downstream thereof. It will be understood that use may also be made of beam-expansion optics with more than two lenses. Normally, however, the input lens of the beam-expansion optics—here the lens 18—is a diverging lens. The lenses 18, 20 of the beam-expansion optics 12 are received in a housing which is not represented in any detail, the converging lens 20 being firmly arranged in the housing, the diverging lens 18, however, being adjustable relative to the converging lens 20 in the direction of the beam axis (denoted by 22). An actuating drive 24 which is controlled by a control unit 26 serves for adjusting the diverging lens 18. The actuating drive 24 is, for example, an electromotive or piezoelectric actuating drive. In a manner not represented in any detail, the actuating drive 24 engages, for example, a lens mount which in turn is movably guided in the housing and supports the diverging lens 18.

The motive travel of the diverging lens 18 in the direction of the beam axis 22 amounts to a few millimeters, for example about 10 mm. The requisite speed of adjustment of the diverging lens 18 may depend, inter alia, on the scan pattern with which the laser beam is guided over the eye to be treated—denoted by 28. It has become evident that with a speed of adjustment of the diverging lens 18 of at least 0.5 m/s, better about 1 m/s, a flap incision can be introduced into the cornea in an acceptably short time. The actuating drive 24 is designed in such a way that it can guarantee this speed of adjustment of the diverging lens 18.

The scanner 14 may contain, in a manner known as such and not represented here in any detail, a pair of deflecting mirrors which enable a targeted deflection of the laser beam in an x-y plane situated perpendicular to the beam axis 22. It is controlled by the control unit 26 in a manner depending on the x-y image of the incision to be introduced into the eye 28 and also in a manner depending on any eye movements. Such eye movements, which in any case are unavoidable in the absence of fixation of the eyeball by means of a suction ring, can be registered by means of an eye-tracking system (eye tracker) indicated schematically as function block 30 and connected to the control unit 26. Systems of such a type are known as such in the specialist field; more detailed elucidations of their function and structure can therefore be dispensed with here. It is sufficient to mention that the eye tracker 30 is able to register eye movements, for example on the basis of a pattern recognition which it carries out in respect of a number of images of the pupil or of another part of the eye that have been recorded one after the other in rapid succession.

The focusing optics 16 are constructed, likewise in a manner known as such, from a plurality of lenses which are not represented here in any detail. The focal length of the focusing optics 16 is fixed. The focusing optics 16 may have been immovably incorporated into the laser device, so that a z-adjustment of the beam focus is possible solely via an adjustment of the diverging lens 18. It is, of course, likewise possible that the focusing optics 16 are adjustably arranged along the beam axis 22, so that a z-adjustment of the beam focus is possible both via an adjustment of the diverging lens 18 and via an adjustment of the focusing optics 16. In the latter case the adjustability of the focusing optics 16 may, for example, be utilised for the purpose of coarse setting prior to the start of the actual operation, whereas the adjustability of the diverging lens 18 is utilised for the setting of the beam focus in differing z-positions during the treatment. In the course of the coarse setting, the diverging lens 18 is expediently held in a central position, so that subsequently in the course of the operation it offers sufficient motive travel in both directions of adjustment.

The laser device according to FIG. 1 further includes a measuring arrangement 32 with which the topography of the corneal surface of the eye 28 can be surveyed. For example, the measuring arrangement operates in accordance with the principle of optical coherence tomography (OCT for short). Suitable evaluating means within the measuring arrangement 32 generate from the measured values topographical measured data that are representative of the topographical profile of the corneal surface, and make the topographical measured data available to the control unit 26. For example, the measuring arrangement 32 may write the topographical measured data to a memory 34 from which the control unit 26 can later retrieve them. This enables a temporally decoupled surveying of the entire corneal topography prior to the actual operation. On the basis of the topographical measured data, the control unit can then firstly compute a two-dimensional actuating profile for the diverging lens 18, which specifies for all scanning points in the x-y plane in each instance a nominal position in which the diverging lens 18 is to be set. In the computation of this actuating profile the control unit 26 takes into account the spacing from the corneal surface in the z-direction (vertical spacing) at which the incision is to be sited at each point in the x-y plane. In the case of the production of a corneal flap, for example, ordinarily a constant thickness of the flap is striven for. Therefore the nominal position of the diverging lens 18 is computed in such a way that the beam focus for all x-y positions of the flap to be produced always has substantially the same z-spacing from the corneal surface (apart from the edges of the flap, where the incision must be guided towards the corneal surface). During the operation it is then sufficient to monitor the z-position of the corneal vertex or/and of at least one other reference point of the eye 28 and to correct the nominal position of the diverging lens 18 resulting from the actuating profile in a manner depending on the currently registered z-position of the reference location of the eye. This monitoring can, where appropriate, likewise be performed by the OCT measuring arrangement 32, which then provides its measured values in this respect to the control unit 26 directly.

The eye 28 is not fixed at all during the treatment or is only fixed with a suction ring which prevents rotational movements of the eyeball. If use is made of a suction ring, the latter is expediently firmly coupled to the focusing optics 16 in the z-direction via a suitable mechanical interface. In each case the treatment is undertaken without a contact lens placed onto the eye 28.

For the production of a surface incision in the cornea, both a line scan and a spiral scan are known. FIGS. 2 and 3 show typical, albeit idealised, progressions of the actuating position of the diverging lens 18 in the case of production of a corneal flap—FIG. 2 for a line scan and FIG. 3 for a spiral scan. In the case of the line scan, where the laser beam is guided over the cornea in lines situated side by side, the diverging lens 18 is moved back and forth continuously, in order to take account of the convexity of the cornea to be overcome in the course of each line. This results in the triangular progression of the actuating position that is shown. Correspondingly, in the case of the line scan the control signal provided by the control unit 26 to the actuating drive 24 has a triangular character. Since the height-difference between line middle and line end in the case of central scan lines, which extend over the middle of the cornea, is greater than in the case of scan lines close to the margin, the triangle height of the control signal varies.

In the case of the spiral scan, on the other hand, a continuous adjustment of the diverging lens 18 in one direction suffices, irrespective of whether the spiral emanates from the centre of the cornea or from the margin. Accordingly, the progression of the lens position shown in FIG. 3 arises, in the form of a monotonically ascending straight line. The control signal provided to the actuating drive 24 will accordingly have a similar character. Since smaller height-differences per unit time have to be overcome in the case of the spiral scan, the spiral scan enables lower traversing speeds of the diverging lens 18 than the line scan. On the other hand, in the case of the spiral scan it has to be taken into account that for a constant spacing of consecutive incision points the pulse-rate of the laser generator 10 for external spiral turns close to the margin has to be set greater than for internal, central spiral turns, provided that the angular velocity of the laser beam remains unchanged.

The invention claimed is:

1. A method of laser surgery on an eye, the method comprising:
   providing a source of pulsed femtosecond laser radiation, a plurality of lenses arranged in succession in the beam path of the laser radiation, of which at least one is arranged so as to be adjustable relative to other lenses in the direction of the beam path, and an actuator for adjusting the at least one adjustable lens;
   measuring a surface topography of a surface of the eye using a measuring arrangement, wherein the measuring arrangement utilizes optical coherence tomography to measure the surface topography of the surface of the eye;
   monitoring a position of the eye relative to the source of pulsed femtosecond laser radiation using the measuring arrangement, wherein the measuring arrangement utilizes optical coherence tomography to monitor the position of the eye relative to the source of pulsed femtosecond laser radiation during an operation on the eye, and wherein the measuring arrangement is configured to determine the current position of the eye relative to the focusing optics during the operation by monitoring a z-position of a reference point on the surface topography of the surface of the eye using optical coherence tomography, wherein the measuring arrangement is configured to communicate data representative of the current position of the eye directly to a control unit configured to control the actuator; and
   controlling, with the control unit, the actuator to move the adjustable lens based on the measured surface topography of the eye obtained in said measuring step using optical coherence tomography and based on the position of the eye as determined in the monitoring step using optical coherence tomography to control a focus depth of the source of pulsed femtosecond laser radiation relative to the surface of the eye.

2. The method of claim 1, wherein the optical coherence tomography of the measuring arrangement has a repetition rate greater than 100 GHz.

3. The method of claim 2, wherein the step of measuring the surface topography of the eye is performed in real-time during a surgical procedure.

4. The method of claim 1, wherein the step of measuring the surface topography of the eye is performed prior to a surgical procedure.

5. The method of claim 1, wherein the step of measuring a surface topography of the surface of the eye and the step of monitoring a position of the eye relative to the source of pulsed femtosecond laser radiation are each performed without any fixation of the eye such that the eye is freely movable with respect to the source of pulsed femtosecond laser radiation.

6. The method of claim 1, wherein the surface of the eye is an outer corneal surface.

7. The method of claim 1, wherein the at least one adjustable lens comprises a diverging lens of beam-expansion optics.

8. The method of claim 7, wherein the at least one adjustable lens further comprises focusing optics positioned after the beam-expansion optics along the beam path.

9. A device for laser-optical eye surgery, comprising:
   a laser source configured to emit a laser beam along a beam path;
   beam-expansion optics in optical communication with the laser source along the beam path, the beam-expansion optics including housing having at least a diverging lens and converging lens mounted therein, wherein the converging lens is fixedly mounted with respect to the housing and wherein the diverging lens is translatable with respect to the housing along the beam path, wherein translation of the diverging lens with respect to the housing adjusts a depth of focus of the laser beam along an axis of the beam path;

an actuator coupled to the diverging lens, the actuator configured to cause translation of the diverging lens with respect to the housing to adjust the depth of focus of the laser beam;

a scanner in optical communication with the beam-expansion optics, the scanner configured to scan the laser beam across positions in a plane that extends perpendicular to the axis of the beam path;

focusing optics having a fixed focal length in optical communication with the scanner, the focusing optics configured to focus the laser beam onto an eye of a patient based on the depth of focus defined by the beam-expansion optics and the positions in the plane perpendicular to the axis of the beam path defined by the scanner;

a measuring system configured to obtain topographical data representing a topography of a corneal surface of the eye utilizing optical coherence tomography and configured to obtain current position information representing a current position of the eye relative to the focusing optics utilizing optical coherence tomography; and a control system in communication with at least the actuator, the scanner, and the measuring system, the control system configured to send z-control signals to the actuator to cause the actuator to translate the diverging lens with respect to the housing to achieve a desired depth of focus along the axis of the beam path, the control system configured to send x-y-control signals to the scanner to cause the scanner to scan the laser beam to desired positions in the plane extending perpendicular to the axis of the beam path, wherein the z-control signals and the x-y control signals are coordinated based on the topographical data and the current position information provided by the measuring system.

10. The device of claim 9, wherein the measuring system is configured to obtain the topographical data and the current position information in real-time during a surgical procedure.

11. The device of claim 10, wherein the measuring system is configured to obtain the topographical data and the current position information without fixation of the eye.

12. The device of claim 10, wherein the measuring system is configured to obtain the topographical data and the current position information with the eye held in a fixed position relative to the focusing optics.

13. The device of claim 9, wherein the current position information representing a current position of the eye relative to the focusing optics includes position information regarding at least one reference location on the corneal surface of the eye.

14. The device of claim 9, wherein the z-control signals supplied to the actuator have a triangular graphical profile with a varying maximum amplitude over time when the laser beam is guided through a plurality of line scans.

15. The device of claim 9, wherein the z-control signals supplied to the actuator have a straight line graphical profile with a constant slope over time when the laser beam is guided through a spiral scan.

16. The device of claim 9, wherein the control system is in communication with the measuring system via a memory unit.

17. The device of claim 9, wherein the measuring system is in communication with the control system such that the topographical data and current position information are provided directly to the control system from the measuring system.

18. The device of claim 9, wherein the measuring system is configured to obtain the current position information representing the current position of the eye relative to the focusing optics by monitoring a z-position of a reference point on the corneal surface of the eye.

* * * * *